United States Patent [19]

Ruggieri et al.

[11] Patent Number: 5,585,502
[45] Date of Patent: Dec. 17, 1996

[54] PROCESS AND PLANT FOR THE PURIFICATION OF RAW MALEIC ANHYDRIDE RECOVERED FROM GASEOUS REACTION MIXTURES

[75] Inventors: Roberto Ruggieri; Sergio Conni, both of Milan, Italy

[73] Assignee: Sisas Societa' Italiana Serie Acetica e Sintetica SpA, Milan, Italy

[21] Appl. No.: 87,854

[22] Filed: Jul. 9, 1993

[30] Foreign Application Priority Data

Feb. 8, 1993 [IT] Italy ................................ MI93A0208

[51] Int. Cl.$^6$ ................................................ C07D 307/36
[52] U.S. Cl. .......................................... 549/262; 549/250
[58] Field of Search ................................... 549/250, 262

[56] References Cited

U.S. PATENT DOCUMENTS

| | | | |
|---|---|---|---|
| 2,942,005 | 6/1960 | Brown et al. | 549/262 |
| 3,891,680 | 6/1975 | Katsumoto et al. | 549/262 |
| 4,118,403 | 10/1978 | White | 549/262 |
| 4,219,388 | 8/1980 | Heller et al. | 549/262 |
| 4,263,211 | 4/1981 | Keunecke et al. | 549/262 |
| 4,282,013 | 8/1981 | Franklin et al. | 549/262 |
| 4,314,946 | 2/1982 | Neri et al. | 549/262 |
| 4,364,748 | 12/1982 | Bakshi | 549/262 |
| 4,370,487 | 1/1983 | Meyer et al. | 549/262 |
| 4,562,283 | 12/1985 | Schnabel et al. | 549/262 |
| 4,571,426 | 2/1986 | Gude et al. | 549/262 |
| 4,961,827 | 10/1990 | Zimmerling et al. | 549/262 |
| 5,026,876 | 6/1991 | Sugawara et al. | 549/262 |
| 5,069,687 | 12/1991 | Bertola et al. | 549/262 |

FOREIGN PATENT DOCUMENTS

| | | | |
|---|---|---|---|
| 722169 | 11/1965 | Canada. | |
| 6508 | 6/1962 | Japan | 549/262 |
| 798456 | 7/1958 | United Kingdom | 549/262 |

*Primary Examiner*—Cecilia Tsang
*Attorney, Agent, or Firm*—Nixon & Vanderhye

[57] ABSTRACT

In the purification of maleic anhydride obtained with an oxidation process, by means of absorption with an organic solvent and fractionation of the resulting liquid phase and purification of the crude maleic anhydride thus separated, the above purification being accomplished through two serially placed fractionating columns, the accumulation of polymerisable acrylic acid overhead the first fractionating column of the purification section, and of water as well as of maleic acid overhead the second fractionating column of the purification section, is avoided by carrying the overhead vapours of said first fractionating column to an absorption tower, preferably operating with the same absorption organic solvent used to absorb the crude maleic anhydride from the reaction mixture, and by carrying the overhead vapours of said fractionating column of said purification section to two condensers placed in series, so that the gaseous fraction, coming out of the first condenser, is fed to said second condenser.

14 Claims, 4 Drawing Sheets

PROCESS AND PLANT FOR THE PURIFICATION OF RAW MALEIC ANHYDRIDE RECOVERED FROM GASEOUS REACTION MIXTURES

The present invention refers to a process for the purification of maleic anhydride and, more particularly, to a process for the purification of the crude maleic anhydride resulting from the recovery by means of absorption with an organic solvent of the same anhydride from gaseous mixtures obtained from butane and/or benzene oxidation.

BACKGROUND OF THE INVENTION

The maleic anhydride is produced by an oxidation reaction in gaseous phase and is obtained as a diluted and raw, gaseous form.

A first recovery method consists in the water absorption of the maleic anhydride, which reacts with water to form maleic acid.

After the water separation by distillation and the dehydration of the maleic acid, maleic anhydride is recovered.

This recovery type involves, however, a high energy consumption, product loss owing to conversion of maleic acid to fumaric acid, high amounts of pollutants in the effluents and frequent plant stops for washings.

Alternatively, for some time the recovery of maleic anhydride by absorption in an organic solvent has been proposed.

To this process, proposed in the U.S. Pat. No. 2,942,005 describing the absorption of maleic anhydride and phthalic anhydride from reaction mixtures, several operating improvements have been brought.

In the U.S. Pat. No. 3,891,680, the gaseous reaction mixture (from which maleic anhydride is to be recovered) is contacted with an organic liquid phase.

A similar process is disclosed in the U.S. Pat. No. 4,118,403, in which the maleic anhydride is recovered by absorption in an organic liquid to which phthalic anhydride is added.

Finally, the U.S. Pat. No. 5,969,687 discloses the maleic anhydride recovery by means of an organic solvent and, in particular, includes a stripping step of the enriched solvent with a gas of low humidity contents to remove water and volatile substances.

In all the procedures based on the use of an organic absorption solvent, the enriched solvent is passed through a separator under vacuum, in which the raw maleic anhydride is condensed overhead and the depleted solvent leaves from the bottom for being recycled to the absorption phase.

As already mentioned, this fractionating step is common to all solvent recovery processes and leads to produce raw maleic anhydride of a 97–99% purity.

The main residual impurities consist of:

(i) a small amount of solvent (ii) a certain amount of organic by-products formed in the oxidation reactor and absorbed together with the maleic anhydride in the absorber, and (iii) water, either free or combined with maleic anhydride.

Typical examples of light organic impurities are acrylic acid and traces of carbonyl compounds.

If the solvent is an ester of a light alcohol (e.g. dibutylphthalate) and the separation between maleic anhydride and solvent is conducted under severe conditions, the alcohol that comes out from the decomposition of the organic solvent might also be present as an impurity in the raw maleic anhydride, typically in the monoester form. Even though the raw maleic anhydride purification can be carried out both in batch and continuous processes, the batch process has some major disadvantages, as for example, the discontinuous steam demand and the necessity of bringing considerable amounts of maleic anhydride to boil, with a consequent, increased risk of exothermal reactions of the maleic anhydride.

The continuous process appears to be preferable and, according to a classical scheme, entails a first fractionating column, within which the light substances are removed, and a second column from the bottom of which the solvent containing a small quantity of maleic anhydride is drawn, that solvent being sent to recycling, whilst the recovered maleic anhydride is drawn in liquid form from the overhead section. However, also the continuous process faces problems and drawbacks not yet solved.

The first of these relates to the drawing of overhead products from the first column where the light substances are separated, including acrylic acid.

The fraction drawn from overhead, and that is sent to a condenser for recycling in liquid phase to the column head, contains acrylic acid in a high concentration, which tends to polymerize and thus to foul the condenser and the column uppermost part in a not negligeable extent.

The second problem connected to the traditional process is represented by water and light or volatile substances present in the second purification column, where the maleic anhydride is recovered in the upper part of the column itself.

This water might originate from atmospheric humidity infiltrating in the vacuum operating system, or from the decomposition of maleic acid present in the raw maleic anhydride. Water may also be possibly produced by losses from condensers or boilers, due to leaking tube-to-tube sheet joints.

Since such water is being absorbed into the maleic anhydride condensed overhead the second purification column and refluxed overhead the column itself, an unwanted concentration increase of water, that is, of maleic acid, in the maleic anhydride obtained in this column, occurs.

Purpose of the present invention is to substantially eliminate such problems and drawbacks.

SUMMARY OF THE INVENTION

This purpose is achieved by the process of the present invention for the purification of raw maleic anhydride coming from a recovery unit, of the type in which the maleic anhydride present in the gaseous reaction mixture is absorbed by means of an organic solvent into an absorber, and the enriched organic solvent is sent to a vacuum separation column, from which raw maleic anhydride is drawn overhead, whereas the depleted solvent is recycled to said vacuum separation column, the maleic anhydride being then sent to a purification section, the process being characterized in that:

(a) the top section of the first purification column is operated under stripping conditions, whereby the vapours drawn overhead are fed to an absorber which is countercurrently fed with an organic solvent, preferably the same solvent used for the absorption of the raw maleic anhydride from the reaction mixture, the solvent phase coming out from this absorber and containing all the maleic anhydride of the overhead section of the first purification column, and most of the acrylic acid being recycled to said first absorption column for absorbing with an organic solvent the raw maleic anhydride from the reaction mixture, and/or (b) the overhead vapour fraction of the second purification column is subjected to a first condensation under conditions such as to cause the condensation of most of the maleic anhydride contained in those vapours, but being kept above the dew point of water present in those vapours, so that the liquid phase recycled to the overhead section of said second purification column will be enriched with liquid maleic arthydride but depleted in water, whilst the vapour phase coming out from said first condensation is sent to a second condensation leading to a liquid phase containing the residual maleic anhydride, a small amount of water and the residual volatile substances, said liquid phase being recycled upstream of the second purification column of the process, in particular to said absorber of raw maleic anhydride from the reaction mixture, or to the feed of raw maleic anhydride at the overhead of said first purification column.

According to a preferred embodiment of the invention, the vapours drawn from overhead the first purification column, before being fed to the absorber, are sent to the inlet of a condenser which can be the same condenser of the vacuum separation column, the raw maleic anhydride being its overhead product, where most of maleic anhydride is condensed.

In turn, the plant according to the invention for the purification of crude maleic anhydride of the type comprising a first column for the absorption with an organic solvent of raw maleic anhydride from the reaction mixture that comes from the oxidation reactor, vacuum separation column fed with the enriched solvent phase coming from said first absorption column, and a purification section fed with the overhead product of said vacuum separation column, said purification section including a first fractionating column and a second purification column, the latter being fed with the bottom liquid going out from said first fractionating column, said plant being characterized in that it comprises:

1) a vacuum absorption tower fed with the overhead gaseous fraction outgoing from said first fractionating column, possibly after partial condensation of said overhead gaseous fraction and/or 2) a first condenser placed at the outlet of the overhead gaseous fraction of said second purification column, and a second condenser placed downstream of said first condenser and fed with the gaseous fraction outgoing from said first condenser.

BRIEF DESCRIPTION OF THE DRAWINGS

The distinctive aspects and advantages of the present invention will be clearer from the following detailed description, related to the enclosed drawings that schematically show a preferred embodiment of the plant for the carrying out of the process of the present invention.

DETAILED DESCRIPTION OF THE INVENTION

Figure 1:
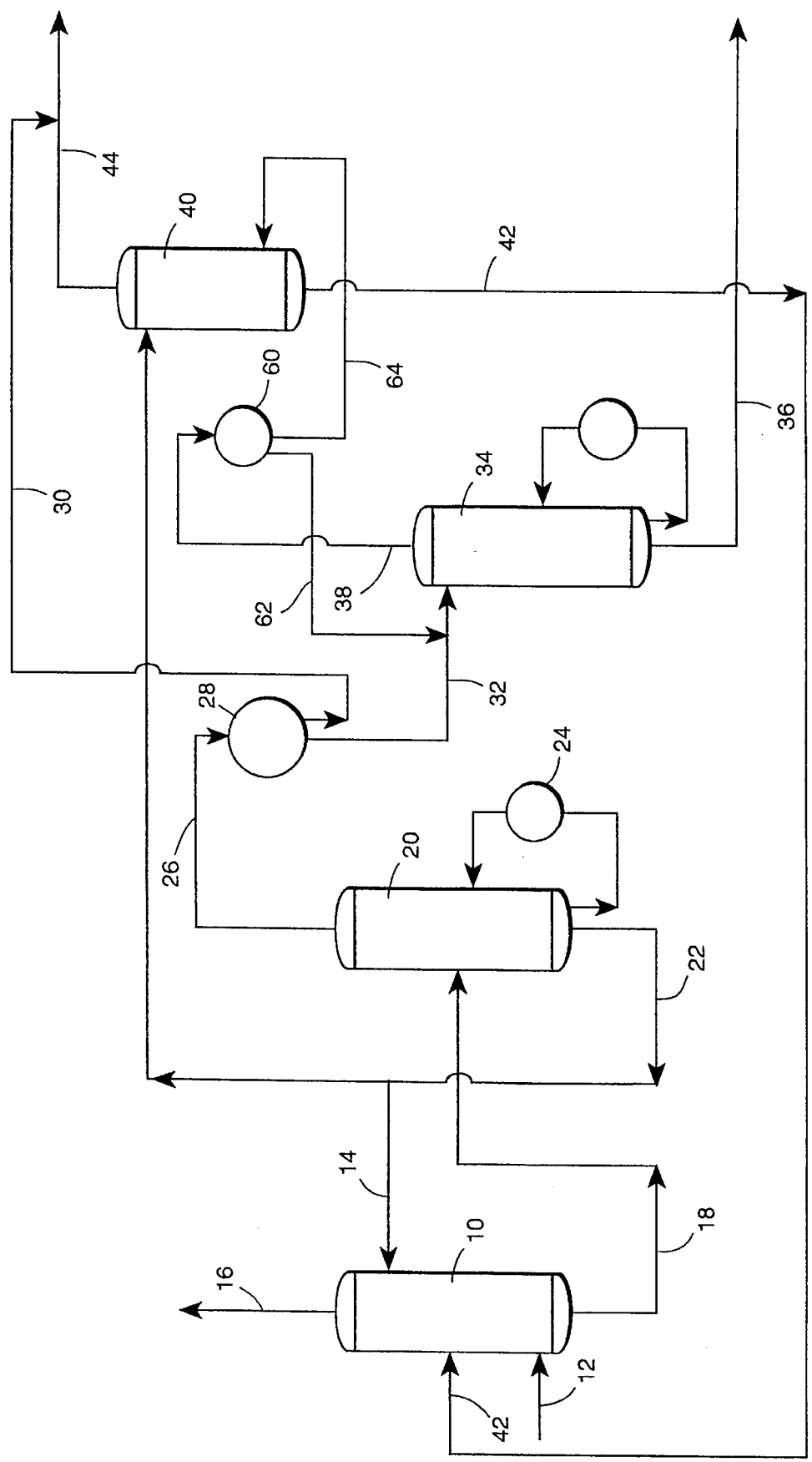
Figure 2:
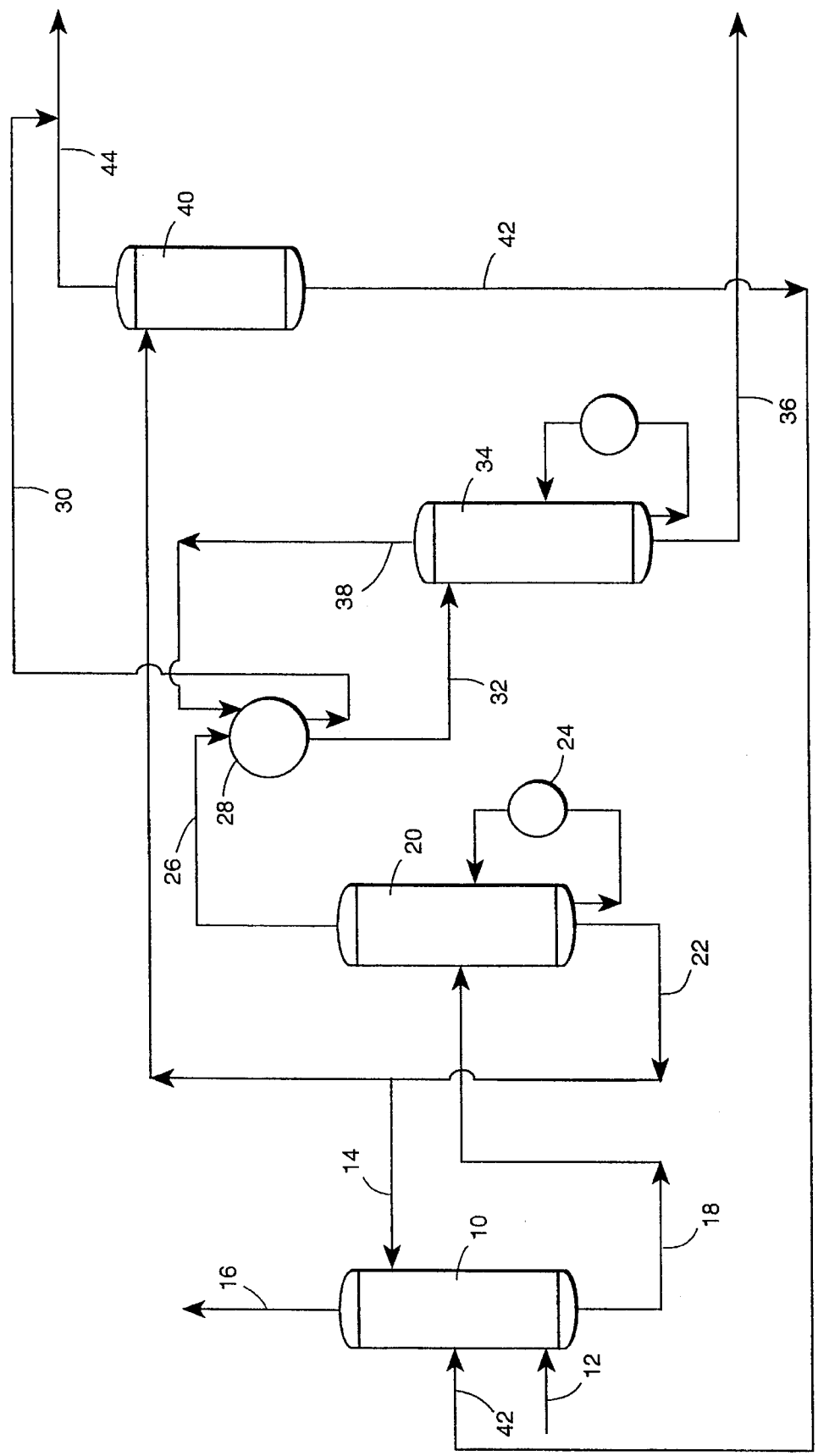
Figure 3:
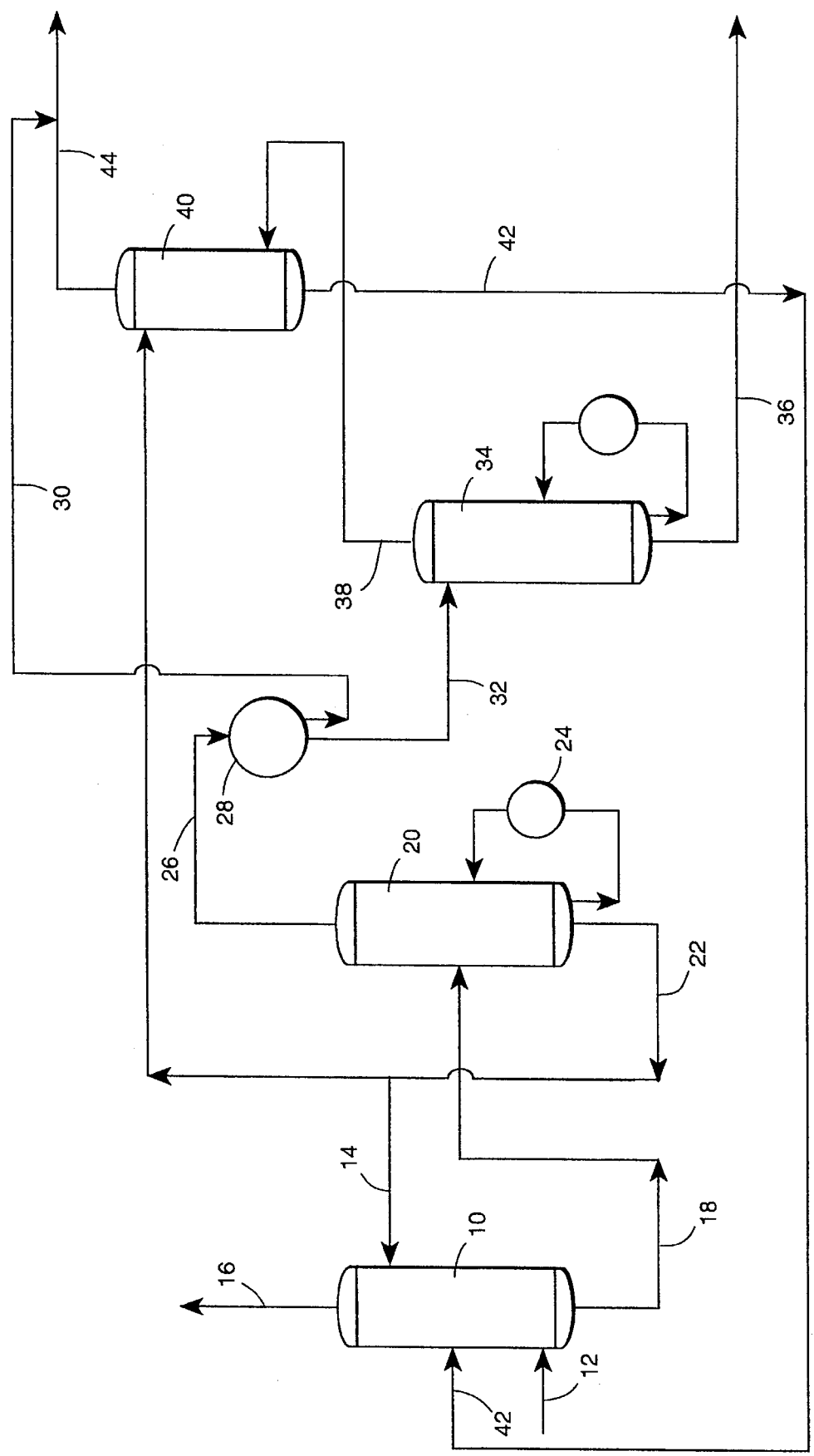
Figure 4:
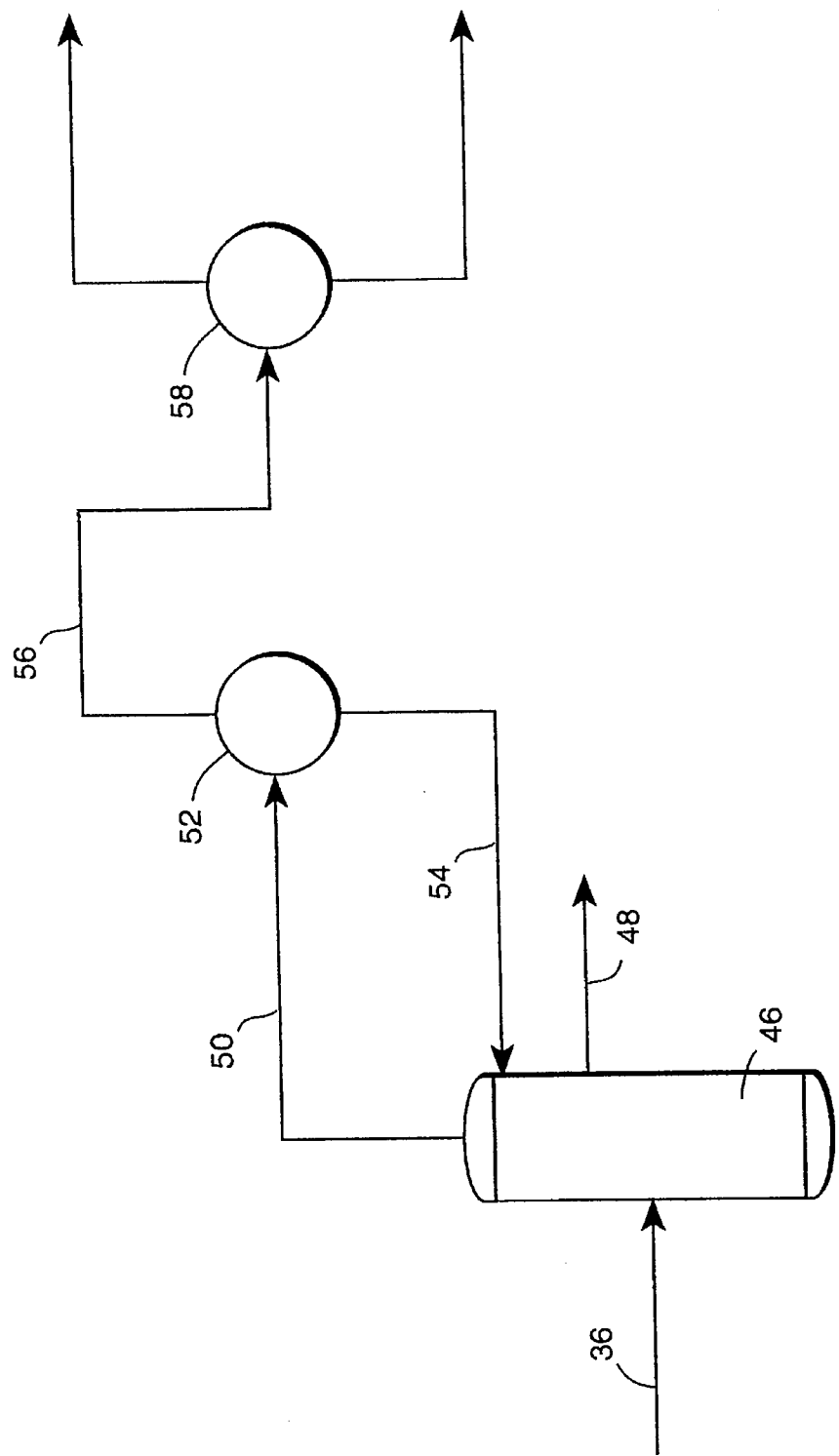

More specifically, FIGS. 1, 2 and 3 show the plant section of the maleic anhydride recovery and of the first part of the purification section, according to possible changes, while FIG. 4 shows the second part of the purification section.

By reference first to the FIG. 3, reference 10 represents the separation column by means of absorption with an organic solvent of the maleic anhydride that comes from the oxidation reactor.

Reference 12 precisely indicates the feed of gaseous mixture coming from the oxidation reactor, whereas reference 14 stands for the feed of the absorption organic solvent.

The exhausted gases are discharged through outlet 16. From the absorber 10, the solvent phase enriched with maleic anhydride is fed, as per reference 18, to a fractionating column 20, from the bottom of which the depleted solvent phase 22 is drawn and recycled to the absorber 10, whilst reference 24 indicates altogether and in general the bottom reboiler of the column 20.

The gaseous phase outgoing from head of the tower 20 is sent, as indicated by reference 26, to a condenser 28, from which a gaseous phase, consisting of uncondensable gases, is obtained and sent for the disposal as shown by reference 30, whilst the condensate (line 32) feeds the first fractionating column 34 of the purification section.

From the bottom of the column 34 a liquid phase 36 is obtained, consisting of maleic anhydride which is sent to the second purification column (as per FIG. 4), while the gaseous or overhead phase, drawn as reference 38 indicates, contains the previously mentioned impurities and, particularly, the acrylic acid that, by polymerisation, solidifies and causes severe scale and fouling problems of the column head 34.

In accordance with the present invention, the above head fraction, instead of being subjected to condensation with recycling of the liquid phase overhead the column 34, is directly sent to a vacuum absorber 40 which, in the embodiment of FIG. 3, is fed by the same organic solvent for the absorption of the raw maleic anhydride from the gaseous reaction mixture in the absorption tower 10, that is, the depleted organic solvent recycled from the bottom of the fractionating column 20.

The bottom fraction deriving from this absorber is sent through line 42 to the first absorbing tower 10 paralleles to the recycle of depleted solvent 14, whilst the overhead fraction, that includes almost mainly uncondensable and volatile products, is sent to the disposal as indicated by reference 44, wherein preferably the gaseous fraction resulting from the condenser 28 also is fed.

It is noteworthy that in this manner the problem related to the presence of no negligible traces of acrylic acid in the raw maleic anhydride is substantially avoided, without however undergoing a loss of maleic anhydride, as much the bottom or liquid fraction from the vacuum absorber 40 passes to the primary absorber 10, where the gaseous reaction mixture subjected to the absorption, operates as a stripping gas to remove the acrylic acid.

In the embodiment form illustrated in FIG. 1, the gaseous or head phase 38 of column 34, before being sent to the vacuum absorption column 40, is partially condensed in a condenser 60, the condensate of which is recycled (through line 62) to the feed 32 of the first fractionating column 34, while the gaseous phase through line 64 is sent to the vacuum absorption column 40.

FIG. 2 shows a change of this embodiment as, instead of a separate condenser 60, there is used the same condenser 28 provided for the condensation of the overhead. product 26 of column 20.

With reference now to FIG. 4, the bottom fraction 36 of the first fractionating column 34 feeds a second fractionating column 46, wherefrom maleic anhydride (as per reference 48), having the desired purity, is obtained, whereas the overhead vapours (reference 50) are sent to a first condenser (reference 52) wherein most of the maleic anhydride contained in these vapours is condensed.

It is important to point out that this condenser is operated under conditions such as not to reach the dew point of water that remains therefore in the vapour phase.

Besides, the apparatus is to be selected of a type with features such as to reduce to the maximum possible extent the contact between uncondensed vapour and condensed liquid.

The condensed liquid, consisting of very pure maleic anhydride and having a very low water content, is recycled (line 54) overhead the column 46, thus reaching the main target, namely to reduce to the maximum possible extent the traces of humidity and of other volatile organic products in the maleic anhydride so produced, and to avoid that water concentration in the purification section increases with the apparent already mentioned disadvantages.

The uncondensed vapours (reference 56), still containing maleic anhydride, water, traces of volatile and colouring substances therein, are condensed in a second condenser 58, in which the liquid phase is condensed at a temperature near to the maleic anhydride melting point, and the liquid stream is recycled upstream along the plant, for example to the primary tower 10 for the absorption of the maleic anhydride from the gaseous reaction mixture or to the feed of the first purification tower 34 together with raw maleic anhydride 32.

In FIGS. 1–3 and 4 enclosed herewith, the preferred embodiment forms of the two parts of the purification section are shown, being understood that it is possible and envisageable to design the purification section with the first fractionating column 34 made as shown in FIGS. 1, 2 or 3, and the second purification column maintained in traditional form and structure or vice versa.

With an industrial plant built up with the variarious of the two purification columns, realized as shown in the drawings, industrial tests of the process in accordance with the invention have been carried out.

The tests have been conducted by checking the concentrations of maleic anthydride, acrylic acid and water at the positions that are typical of the plant and of the related process.

The data, referred to 1000 kg/h of treated raw maleic anhydride are reported in the following table

TABLE I

|  | Maleic anhydride | Acrylic Acid | Water (as free water and maleic acid) |
| --- | --- | --- | --- |
| Raw maleic anhydride | 1000 | 2.34 | 4.78 |
| purification column (34) - overhead | 200 | 2.12 | 4.40 |
| purification column (34) - bottom | 800 | 0.22 | 0.34 |
| air leakages entering the column (46) | — | — | 0.37 |
| gaseous phase from condenser (52) | 25 | 0.19 | 0.51 |
| liquid from condenser (58) | 23 | 0.12 | 0.27 |
| exhaubt gas from condenser (58) | 2 | 0.07 | 0.24 |
| final product (48) | 750 | 0.03 | 0.20 |

From the data of the previous table it is clear that in the overhead fraction of the first purification column, about 20% of the maleic anhydride to be purified is present together with a large part of the acrylic acid and water.

In the subsequent steps, more than 99% of this maleic anhydride is recovered (particularly in the vacuum absorption tower 40). In addition, the uncondensable vapours from the outlet of the first condenser 52 contain most of the water and of the acrylic acid which are fed to the second purification column 46.

These vapours are condensed in the second condenser and recycled upstream so as to extract the light components.

With the process and plant of the invention, the purified maleic anhydride has an acrylic acid content definitely lower than 0.01% and a maleic acid content definitely lower than 0.05%, whereas with the traditional processes and plants, the acrylic acid content may be about 0.01% or higher, and that of maleic acid may be about 0.05% or more.

Table 2 indicates the typical values for a traditional purification section, operated without using the process of the invention, wherein from overhead the first column a liquid and a gaseous phase are extracted and the second column is equipped with only one condenser for the overhead product.

Also for this table the reported data refer to a 1000 kg/h feed of raw maleic anhydride.

TABLE II

|  | Maleic anhydride | Acrylic acid | Water (as free water and maleic acid) |
| --- | --- | --- | --- |
| Raw maleic anhydride | 1000 | 2.34 | 4.78 |
| purification column (34) - overhead (liq. + vap.) | 20 | 2.10 | 4.35 |
| purification column (34) - bottom | 980 | 0.24 | 0.39 |
| leakages in (46) | — | — | 0.37 |
| exhaust gas from the only condenser of column (46) | 2.8 | 0.10 | 0.24 |
| final product | 950 | 0.14 | 0.52 |

We claim:

1. A process for the purification of raw maleic anhydride coming from a recovery unit, of the type wherein the gaseous reaction mixture is subjected to separation by absorption in a first absorber of the raw maleic anhydride by means of an organic solvent and, the enriched organic solvent is sent to a vacuum separation column, from overhead of which raw maleic anhydride is drawn, whilst the depleted solvent is recycled to said separation column, the raw maleic anhydride being subsequently sent to a purification section that consists of two serially placed fractionating columns characterized in that the top part of the first purification column is operated under stripping conditions, whereby the overhead vapors are drawn and fed to a second absorber which is in turn fed countercurrently with an organic solvent, the solvent phase from the outlet of said second absorber, containing all the maleic anhydride present in the overhead fraction of the first purification column and a large portion of the acrylic acid, being recycled to said first absorber for the absorption with an organic solvent of the crude maleic anhydride from the reaction mixture.

2. A process according to claim 1, characterized in that the vapors drawn from overhead said first purification column, before being recycled to said first absorber, are sent to a condenser, operating under conditions for the condensation of the raw maleic anhydride.

3. A process according to claim 2, characterized in that said condenser is placed in series with said separation column and downstream of same.

4. A process for the purification of raw maleic anhydride, of the type wherein the gaseous reaction mixture is subjected to separation by absorption in a first absorber of the raw maleic anhydride by means of an organic solvent and the enriched organic solvent is sent to a vacuum separation column, from overhead of which raw maleic anhydride is drawn, whilst the depleted solvent is recycled to said first absorber, the raw maleic anhydride being subsequently sent to a purification section consisting of two serially placed fractionating columns, characterized in that the gaseous head fraction of the second purification column is subjected to a first condensation, under conditions such as to cause the condensation of most of the maleic anhydride contained in such vapors, but being kept above the dew-point of the water present in such vapors, so that the liquid phase, recycled to the overhead section of said purification column, is enriched in liquid maleic anhydride but depleted of water and other light components whereas the vapor phase outgoing from said first condensation is sent to a second condensation, thus obtaining a liquid phase containing the residual maleic anhydride, a small amount of water and the residual volatile products, said liquid phase being recycled upstream the purification section of the process.

5. A process according to claim 4, characterized in that said liquid phase, recycled upstream the purification section, is recycled to said first absorber of raw maleic anhydride from the reaction mixture or to the feed of the raw maleic anhydride to said first purification column.

6. A process according to claim 1, characterized in that said organic solvent, used in said second absorber fed with the overhead product of said first purification column, is the same solvent used for the absorption of the raw maleic anhydride from the reaction mixture in the first absorber.

7. A plant for the purification of raw maleic anhydride, of the type which comprises a first absorber for the absorption with an organic solvent of raw maleic anhydride from the reaction mixture coming out from the oxidation reactor, a vacuum separation column fed with the enriched solvent phase, coming out of said first absorber, and a purification section fed with the overhead phase of said separation column, said purification section including a first fractionating column and a second fractionating column, fed with the bottom liquid product from the outlet of said first fractionating column, characterized by comprising a second absorber fed with the overhead gaseous fraction coming out of said first fractionating column, the liquid phase, consisting of solvent and maleic anhydride as well as of acrylic acid that comes from the bottom of said second absorber, being recycled to said first absorber for the absorption of raw maleic anhydride from said gaseous reaction mixture.

8. A plant for the purification of raw maleic anhydride, of the type comprising a first absorber for the absorption with an organic solvent of raw maleic anhydride from the reaction mixture that comes out from the oxidation reactor, a vacuum separation column fed with the enriched solvent phase coming from said first absorber and a purification section fed with the overhead phase of said separation column said purification section including a first fractionating column and a second fractionating column fed with the bottom liquid product from the outlet of said first fractionating column, characterized in that it comprises a first and a second condenser, placed at the outlet of the overhead gaseous fraction of said second fractionating column of the purification section, said second condenser being fed with the gaseous fraction coming out from said first condenser.

9. A plant according to claim 8, characterized in that purified maleic anhydride is obtained from said second fractionating column of the purification section, and the liquid phase derived from said second condenser is recycled upstream the purification section.

10. A plant according to claim 9, characterized in that said liquid phase from the outlet of said second condenser is recycled to said first absorber for the absorption with an organic solvent of the raw reaction mixture or to said first fractionating column of said purification section.

11. A plant according to claim 7 characterized in that said overhead gaseous fraction coming out from said first fractionating column of said purification section is sent to a condenser for an at least partial condensation thereof.

12. A plant according to claim 7, characterized in that said overhead gaseous fraction is sent to a condenser placed at the outlet of the overhead gaseous product of said second under-vacuum separation column for an at least partial condensation thereof.

13. A process for the purification of raw maleic anhydride, comprising the steps of:

contacting a gaseous reaction mixture comprising maleic anhydride with an organic solvent in a first absorber to produce an organic solvent enriched in maleic anhydride;

forwarding said enriched organic solvent to a vacuum separation column;

withdrawing from overhead of said column raw maleic anhydride;

recycling solvent depleted of maleic anhydride to said first absorber;

forwarding said raw maleic anhydride to a fractionating column operated under stripping conditions whereby overhead vapors from said fractionating column are fed to a second absorber which is fed countercurrently with an organic solvent; and recycling to said first absorber a solvent phase from an outlet of said second absorber containing maleic anhydride and acrylic acid present in the overhead fraction of said purification column.

14. A plant for the purification of raw maleic anhydride, comprising:

a first absorber in which a reaction mixture from an oxidation reactor comprising raw maleic anhydride is contacted with an organic solvent;

a vacuum separation column for receiving solvent enriched with maleic anhydride from said first absorber;

a purification section for receiving an overhead phase of said vacuum separation column, said purification section including first and second fractionating columns, said second fractionating being fed with bottom liquid product from an outlet of said first fractionating column; and a vacuum absorption tower for receiving an overhead gaseous fraction from said first fractionating column.

* * * * *